United States Patent
Rastogi et al.

(10) Patent No.: US 7,250,197 B2
(45) Date of Patent: Jul. 31, 2007

(54) PLASMA TREATMENT OF CONTACT LENS AND IOL

(75) Inventors: Sanjay Rastogi, Rochester, NY (US); Michael J. Moorehead, Fairport, NY (US); William J. Appleton, Rochester, NY (US); George L. Grobe, III, Fort Wayne, IN (US); Paul Trotto, Honeoye Falls, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 470 days.

(21) Appl. No.: 10/647,556

(22) Filed: Aug. 25, 2003

(65) Prior Publication Data

US 2005/0045589 A1    Mar. 3, 2005

(51) Int. Cl.
*B05D 5/00*    (2006.01)
*B05D 3/06*    (2006.01)
*B05D 3/14*    (2006.01)
*B05D 3/10*    (2006.01)
*B05D 5/04*    (2006.01)

(52) U.S. Cl. .................... 427/539; 427/535; 427/534; 427/164

(58) Field of Classification Search .................... None
See application file for complete search history.

(56) References Cited

U.S. PATENT DOCUMENTS

| | | | |
|---|---|---|---|
| 4,055,378 A | 10/1977 | Feneberg et al. | |
| 4,096,315 A * | 6/1978 | Kubacki | .................... 428/412 |
| 4,122,942 A | 10/1978 | Wolfson | |
| 4,143,949 A | 3/1979 | Chen | |
| 4,168,112 A | 9/1979 | Ellis et al. | |
| 4,214,014 A | 7/1980 | Hofer et al. | |
| 4,287,175 A | 9/1981 | Katz | |
| 4,312,575 A | 1/1982 | Peyman et al. | |
| 4,321,261 A | 3/1982 | Ellis et al. | |
| 4,436,730 A | 3/1984 | Ellis et al. | |
| 4,632,844 A | 12/1986 | Yanagihara et al. | |
| 5,211,759 A * | 5/1993 | Zimmermann et al. | . 118/723 R |
| 5,397,848 A | 3/1995 | Yang et al. | |
| 5,503,515 A * | 4/1996 | Moorehead | .................. 414/755 |
| 5,645,882 A * | 7/1997 | Llanos | ....................... 427/2.24 |
| 5,700,559 A | 12/1997 | Sheu et al. | |
| 5,705,583 A | 1/1998 | Bowers et al. | |
| 5,807,636 A | 9/1998 | Sheu et al. | |
| 5,874,127 A * | 2/1999 | Winterton et al. | ........... 427/164 |
| 5,969,793 A | 10/1999 | Dobner | |
| 6,025,013 A * | 2/2000 | Heming et al. | ................. 427/9 |
| 6,193,369 B1 * | 2/2001 | Valint et al. | ............. 351/160 H |
| 6,213,604 B1 * | 4/2001 | Valint et al. | ................. 351/177 |
| 6,502,879 B1 | 1/2003 | Miyazawa | |
| 6,581,761 B1 * | 6/2003 | Stafford et al. | ............... 206/5.1 |

(Continued)

FOREIGN PATENT DOCUMENTS

EP    0963761 A1    12/1999

(Continued)

*Primary Examiner*—Marianne Padgett

(57) ABSTRACT

Intraocular lenses or contact lenses 20 are placed on a lower spindle 34 and held there by a vacuum in conduit 34. Noble and reactive gases 56, 58 are introduced and a voltage is applied across upper spindle 32 and lower spindle 34 to plasma treat one surface of the lens. The lens is transferred to the other spindle and the process is repeated.

24 Claims, 3 Drawing Sheets

U.S. PATENT DOCUMENTS

| | | |
|---|---|---|
| 6,610,350 B2 | 8/2003 | Suzuki et al. ............... 427/2.24 |
| 6,916,512 B2 * | 7/2005 | Danielzik et al. ........... 427/585 |
| 2005/0208512 A1 * | 9/2005 | Jallouli et al. .............. 427/169 |

FOREIGN PATENT DOCUMENTS

| | | |
|---|---|---|
| EP | 1180429 A2 | 2/2002 |
| EP | 1201253 B1 | 4/2004 |
| WO | WO 94/29756 A2 | 12/1994 |
| WO | WO 95/04609 A1 | 2/1995 |

\* cited by examiner

PLASMA TREATMENT OF CONTACT LENS AND IOL

FIELD OF THE INVENTION

The present invention is directed to the surface treatment of medical devices including ophthalmic lenses such as intraocular lenses and contact lenses. In particular, the present invention is directed to a more efficient process for plasma treating surface of intraocular lenses or contact lenses.

BACKGROUND

Contact lenses and intraocular lenses made from silicone-containing materials have been investigated for a number of years. Such materials can generally be subdivided into two major classes, namely hydrogels and non-hydrogels. Non-hydrogels do not absorb appreciable amounts of water, whereas hydrogels can absorb and retain water in an equilibrium state. Regardless of their water content, both non-hydrogel and hydrogel silicone medical devices tend to have relatively hydrophobic, non-wettable surfaces that have a high affinity for lipids. This problem is of particular concern with contact lenses.

Those skilled in the art have long recognized the need for modifying the surface of such silicone contact lenses so that they are compatible with the eye. It is known that increased hydrophilicity of the contact lens surface improves the wettability of the contact lenses. This in turn is associated with improved wear comfort of contact lenses. Additionally, the surface of the lens can affect the lens's susceptibility to deposition, particularly the deposition of proteins and lipids from the tear fluid during lens wear. Accumulated deposition can cause eye discomfort or even inflammation. In the case of extended wear lenses (i.e. lenses used without daily removal of the lens before sleep), the surface is especially important, since extended wear lens must be designed for high standards of comfort and biocompatibility over an extended period of time.

Silicone lenses have been subjected to plasma surface treatment to improve their surface properties, e.g., surfaces have been rendered more hydrophilic, deposit resistant, scratch-resistant, or otherwise modified. Examples of previously disclosed plasma surface treatments include subjecting contact lens surfaces to plasma comprising an inert gas or oxygen (see, for example, U.S. Pat. Nos. 4,055,378; 4,122,942; and 4,214,014); various hydrocarbon monomers (see, for example, U.S. Pat. No. 4,143,949); and combinations of oxidizing agents and hydrocarbons such as water and ethanol (see, for example, WO 95/04609 and U.S. Pat. No. 4,632,844). U.S. Pat. No. 4,312,575 to Peyman et al. discloses a process for providing a barrier coating on a silicone or polyurethane lens by subjecting the lens to an electrical glow discharge (plasma) process conducted by first subjecting the lens to a hydrocarbon atmosphere followed by subjecting the lens to oxygen during flow discharge, thereby increasing the hydrophilicity of the lens surface.

U.S. Pat. Nos. 4,168,112, 4,321,261 and 4,436,730, all issued to Ellis et al., disclose methods for treating a charged contact lens surface with an oppositely charged ionic polymer to form a polyelectrolyte complex on the lens surface that improves wettability. U.S. Pat. No. 4,287,175 to Katz discloses a method of wetting a contact lens that comprises inserting a water-soluble solid polymer into the cul-de-sac of the eye. The disclosed polymers include cellulose derivatives, acrylates and natural products such as gelatin, pectins and starch derivatives. U.S. Pat. No. 5,397,848 to Yang et al. discloses a method of incorporating hydrophilic constituents into silicone polymer materials for use in contact and intra-ocular lenses. U.S. Pat. Nos. 5,700,559 and 5,807,636, both to Sheu et al., discloses hydrophilic articles (for example, contact lenses) comprising a substrate, an ionic polymeric layer on the substrate and a disordered polyelectrolyte coating ionically bonded to the polymeric layer. U.S. Pat. No. 5,705,583 to Bowers et al. discloses biocompatible polymeric surface coatings. The polymeric surface coatings disclosed include coatings synthesized from monomers bearing a center of positive charge, including cationic and zwitterionic monomers. European Patent Application EP 0 963 761 A1 discloses biomedical devices with coating that are said to be stable, hydrophilic and antimicrobial, and which are formed using a coupling agent to bond a carboxyl-containing hydrophilic coating to the surface by ester or amide linkages.

Plasma treating operations are performed in large, batch process reactors. In one prior art method, contact lenses requiring surface treatment are dry-released from the anterior mold and edged polished, if necessary. The lenses are placed manually by a worker concave-side up into a transfer tray. The transfer tray contains a plurality of cylindrical cavities with flat bottoms and is typically made from white polystyrene having a matte finish. The lens diameter is typically smaller than the diameter of the cavity so that the lens is easily placed and retrieved from the tray. The lenses are taken to a different workstation for surface treatment. At the surface treatment station (e.g. using commercial Metroline Plasma Deposition Model Number 7100 Series Chamber), lenses are inverted onto a surface treatment tray such as the removable shelf supplied with the Metroline Plasma Chamber. The Metroline shelf has a plurality of small, spaced perforations located at predetermined intervals, each of the perforations having diameters substantially smaller than any one of the lenses. Each lens is placed on the shelf, concave-side down. The lenses are plasma reacted and inverted, e.g. using a manual method or using a semi-automated device such as an air knife as disclosed in U.S. Pat. No. 5,503,515 (Moorehead, assigned to Bausch & Lomb Incorporated). Unfortunately, it has been found that when lenses are initially inverted from the transfer tray onto the Metroline shelf, placement of the lenses is random with the individual lens not necessarily over a perforation as intended. If an individual lens is not situated over a perforation, the lens will not invert. Instead, a worker must use tweezers to turn the lens over. The other side of the lens is then subjected to a plasma reaction. The surface treatment requires two cycles of plasma reaction. The lenses are then picked up by a worker using tweezers and transferred for other processing such as extraction. The worker is integral to this whole process, especially in making sure all the lenses invert over the air knife and transferring the surface treated lenses for extraction.

Others have shown apparatus for individually handling lens. For example, U.S. Pat. Nos. 5,969,793 and 6,502,879 show apparatus for removing individual lenses from molds and for transferring the lenses to other process apparatus. It is also known that a lens may have its edge polished while the lens is supported on a spindle and the edge polishing tool is moved in relation to the spindle. See U.S. Pat. App. Pub. 2002/0115389 published Aug. 22, 2002.

Thus, it is desired to provide a plasma process for treating the surfaces of silicone hydrogel contact lens with an optically clear, hydrophilic surface film that will not only exhibit improved wettability, but which will generally allow the use of a silicone hydrogel contact lens in the human eye for extended period of time. There is also an unmet need for a more efficient process that plasma treats lenses one at a time in sequence with the edge polishing step. In the case of a silicone hydrogel lens for extended wear, it would be desirable to provide a contact lens with a surface that is also highly permeable to oxygen and water. Such a surface treated lens would be comfortable to wear in actual use and would allow for the extended wear of the lens without irritation or other adverse effects to the cornea. It would be desirable to manufacture such a surface treated lens without the need for an oxidation step such as plasma treatment or corona discharge treatment.

SUMMARY

The invention provides a process and an apparatus for plasma treating contact lens. The invention overcomes drawbacks of conventional batch processing by either individually plasma treating each lens, or by treating multiple lenses with multiple plasma generators. The individual treatment process uses a spindle apparatus that has upper and lower spindles for carrying a lens trough a series of process stations, including a plasma treatment station. The spindles support one surface of a contact lens and expose the other surface of the lens to plasma treatment that will render the surface of the lens more wettable, scratch resistant, or improved in other ways. The other surface of the lens is treated by transferring the lens to another spindle to support the treated surface of the contact lens and to expose the other surface of the contact lens to the plasma treatment process. The plasma is a glow discharge that is generated proximate the exposed surface of the contact lens.

Prior to entering the plasma station, the lens passes through an edge polishing station. After polishing, debris is removed by a blast of air or other suitable fluid. In general, a contact lens has a concave posterior surface and a convex anterior surface. In order to support the lens, one spindle has a convex surface and the other spindle has a convex surface. The spindles have openings in their surfaces that are in fluid communication with a vacuum or pressure source for holding or discharging the lens from the surface of the spindle. The lens is treated for a short time, less than a minute and possibly as short as ten seconds. During plasma treatment the exposed surface of the lens is surrounded by a glow discharge that is generated from inert gas and a reactive gas. For example, argon with hydrogen peroxide provides a noble gas and oxidizing plasma. The spindle holding the lens is grounded and the other spindle (or suitable electrode) if positively charged. The plasma may be generated by DC or AC voltages. Because only one lens at a time is treated, the power requirements are lower than conventional large scale batch plasma processes. The invention may be practiced at atmospheric or reduced pressure. At atmospheric pressure the treatment station may be open to the atmosphere or enclosed in a chamber isolated from atmosphere.

The invention also processes multiple lenses using multiple plasma generators by simultaneously plasma treating multiple contact lens that travel along a treatment path. The method supports the lenses with a support tray to expose one of the surfaces of the lens to the plasma treatment process. The invention provides for moving the lenses and the plasma generators with respect to one another or for keeping the two together. In either case, a key step is generating a first glow discharge proximate the lens path for treating the exposed surface of the contact lenses. After one surface is finished, the lenses are rotated to expose the other surface and it is likewise treated in a similar manner. The invention contemplates using the same plasma generator for treating both sides of the lens, or for providing a second plasma generator station for treating the other surface after rotation.

The apparatus may include a plurality of elongated plasma heads arranged transverse or parallel to the process path. As an alternative, the apparatus may also comprise an array of plasma heads that corresponds to the number of lenses that are simultaneously treated. Again, the treatment time is shorter than treatment in a batch process because each lens either has its own plasma generator (the array), the lens travels in line with a plasma head, or the lens travels transverse to a number of linear plasma heads.

DRAWINGS

DETAILED DESCRIPTION

Figure 1:
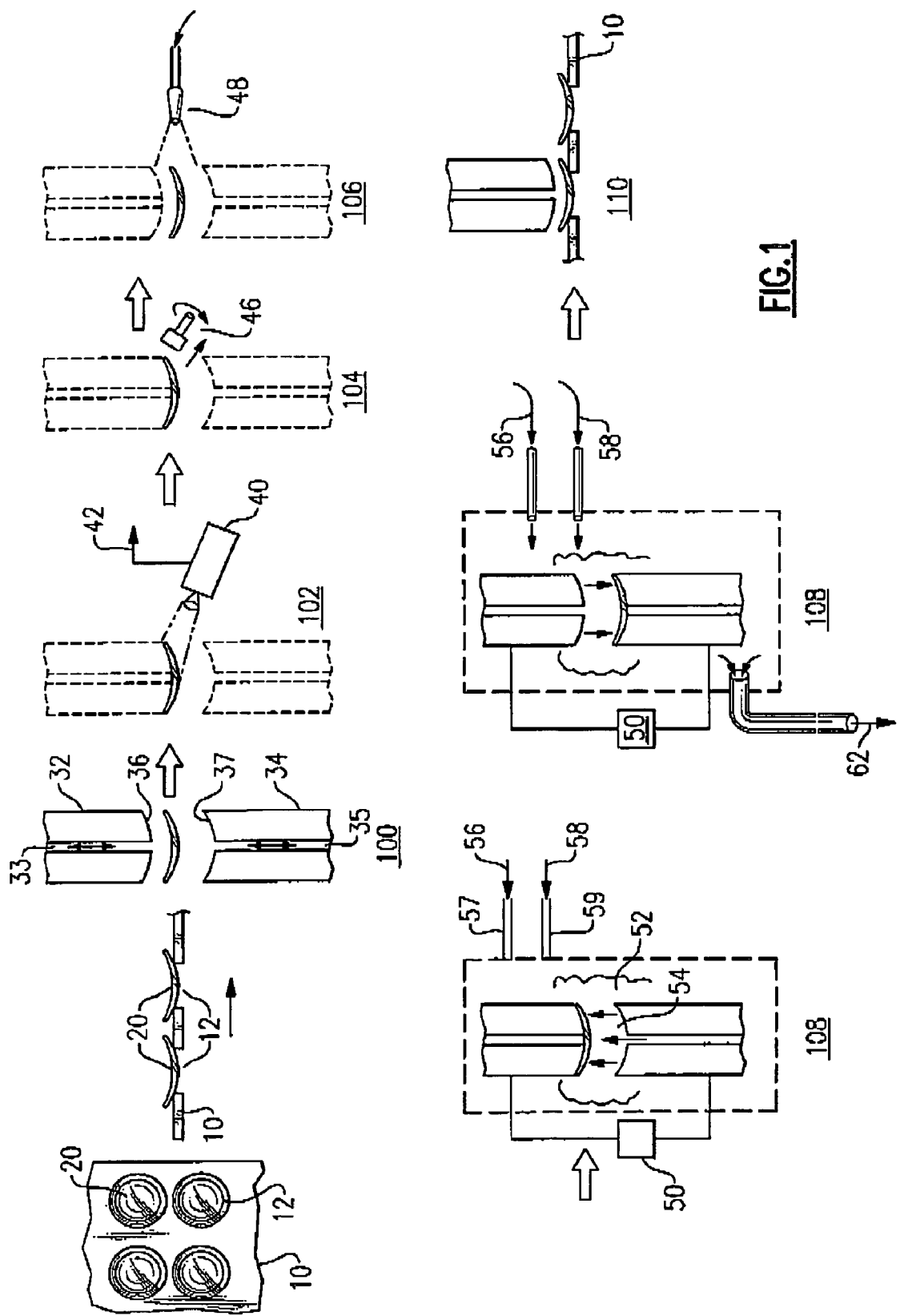
FIG. 1 shows a process path for individual lens processing.

The process path for lenses 20 is shown in FIG. 1. A support tray 10 has a number of openings 12 defined by circular walls 13. The diameter of the openings 12 is smaller than the diameter of the lens. The contact lenses 20 are carried in the tray 10 supported by the circular walls 13 that define the openings 13.

A lens treatment process has a number of stations for treating the formed lens. As shown in FIG. 1 there are stations 100, 102, 104, 106, and 108 that perform process operations described later in detail. The lens travels from one process station to the next along a treatment path by a spindle apparatus (not shown). The spindle apparatus has an upper spindle 32 with a convex surface 36 for contacting the posterior surface of the lens 20. A fluid chamber 33 in the body of the upper spindle 32 receives a vacuum signal to hold the lens on the convex surface 36 and a pressure signal to discharge the lens 20 from the surface 36. The lower spindle 34 has a concave surface 37 for supporting and holding the anterior surface of the lens 20. A fluid chamber 35 in the body of the lower spindle 34 receives a vacuum signal to hold the lens 20 on the concave surface 37 and a pressure signal to discharge the lens 20 from the surface 37.

Those skilled in the art understand that the upper and lower spindles 32, 34 may form a coordinated pair of lens carriers for carrying the lens 20 from one station to the next. The upper and lower spindles 32, 34 move in a vertical direction to engage and disengage with a lens and transfer the lens between spindles. The spindles also translate to move a lens from one process station to the next. As an alternative, the spindles may be mounted on a carousel that rotates to move the lens from one process station to the next. Two or more carousels may be used in tandem and lenses are transferred from one carousel to the next at adjacent transfer stations. The spindle at the transfer station translates the lens from one carousel to the next. In this manner the lens is operated upon individually at each process station and does not undergo a batch process step with other lenses.

At a first process station 100 the lens 20 is removed from the tray 10 by the upper spindle 36. At station 102 the lens is visually inspected for defects. A camera or other suitable apparatus 40 captures an image of the lens 20 and outputs the image via a path 42 to a display (not shown). An operator or suitable pattern recognition software inspects the image. If the lens is free of defects, it is further processed; otherwise it is discarded. At the next station 104, the edge of the lens is polished by an edge finishing tool 46. The tool moves relative to the edge of the lens to finish the edge so that the edge is comfortable for a user. After the edge is polished, the lens 20 moves to the cleaning station 106 where a forced jet of air or cleaning fluid from nozzle 48 blows away any debris remaining from the prior polishing operation.

The next station in the process line is plasma surface treatment station 108. Here the lens 20 is treated with suitable plasma 54 to impart desired properties to the surface of the lens. As described above, it is well known that oxidizing plasmas improve the wettability of lens 20. Other plasma treatments improve scratch resistance. Station 108 uses the upper spindle 32 s one electrode and the lower spindle 34 as the other electrode. It is contemplated that electrodes other than spindles may be used. However, if the spindles are employed and available, using them as electrodes is more efficient. The spindles 32, 34 are connected to an electrical source 50 that generates either DC or AC voltage. The AC voltage applied may be in the microwave range or any other suitable frequency depending upon the desired plasma treatment process. At station 108 suitable noble and reactive gases 56, 58 are introduced. Under the influence of the applied voltage, the gas at the station begins to glow and plasma 52 is generated.

The plasma 52 includes active particles, electrons, and free radical that are directed from one spindle to the surface of the lens 20. Conduit 62 removes the gaseous reaction products. Because only one lens is processed in the plasma, process time is relatively short, i.e., less than one minute. In one embodiment, the plasma treatment station 108 is operated at atmospheric pressure. The noble gas, such as argon, envelopes the region between the spindles and effectively shields the region from ambient atmosphere. However, if desired, the plasma station 108 may be disposed in a sealed chamber with suitable entrance and exit load locks. The lens may be transferred between spindle surfaces 36, 37 and the plasma operation repeated to apply the plasma treatment to the other surface of the lens 20. After all plasma processes are completed, the lens is moved to a holder tray 10 where other lenses are also stored. The lenses in tray 10 may then be moved to a final inspection and packaging station (not shown).

Figure 2:
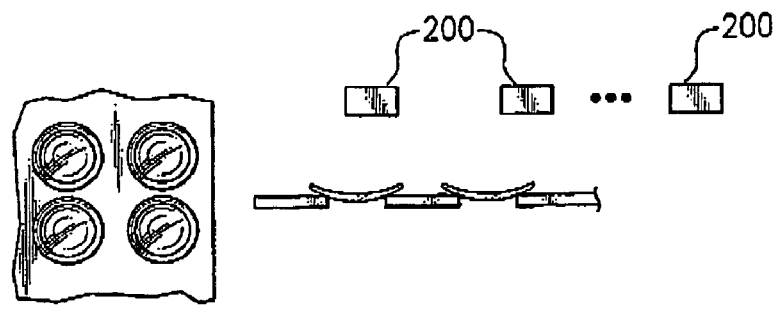
FIG. 2 shows a plasma process path with multiple plasma generators.
Figure 3:
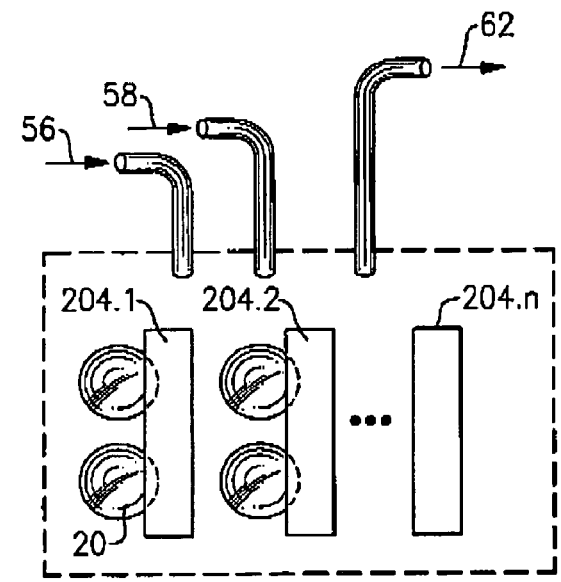
FIG. 3 shows a process path with plasma generators arranged transverse to the process path.
Figure 4:
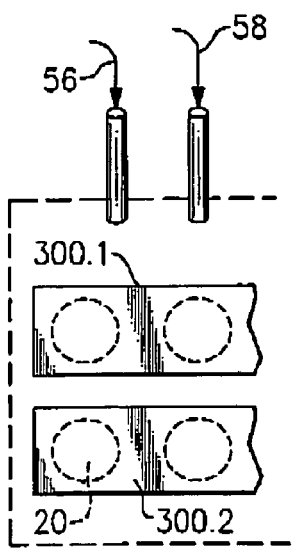
FIG. 4 shows a process path with plasma generators arranged parallel to the process path.
Figure 5:
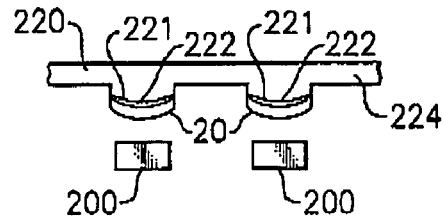
FIG. 5 shows a revering tray for carrying lenses past an array of plasma generators.

As an alternate technique, multiple lenses are simultaneously processed by multiple plasma heads and moving lenses. For example, FIG. 2 depicts a plasma process path with multiple plasma generating heads 200. In the general embodiment shown in FIG. 3, the lenses 20 are carried on a tray and pass through a plurality of plasma generating heads 204.1, 204.2 and 204.n. The generating heads are arranged transverse or parallel to the path of the lens. The tray is carried past the generating heads along a path by a conveyor belt or other suitable translating means (not shown). The generating heads may be arrayed as a sequential series of bars 204.1, 204.2, 204.n, disposed across the path of the lenses, as shown in FIG. 4. The heads could be bars 301.1, 301.2, 301.n, arrayed parallel to the path of the lenses in line with the path of the lenses, as shown in FIG. 4. At the end of the path, the lenses are turned over and their other sides are likewise plasma treated. As an alternative, the lenses 20 could be picked up by an array of spindles or a transfer plate 220 (see, FIG. 5) and the anterior surfaces could be plasma treated in line. The transfer plate 220 has convex surfaces 221 with apertures 222.

Those skilled in the art understand that the lenses may move relative to the plasma generating heads or remain stationary beneath them. The relative motion or lack is not important. What is important is the time spent in the plasma. That time must be sufficient to achieve the desired purpose and it may be found empirically. It is expected that the time will be less than the time required for batch processing because of the multiple plasma generating heads.

A vacuum is drawn through a manifold 224 in the plate that communicates with the apertures. Once the lenses are on the transfer plate, their anterior surface may be plasma processed. The lenses could be reversed in direction. The in-line multiple head plasma array may operate at atmospheric pressure. It likewise has inlets of inert and reactive gases and an outlet for reactive products. The apparatus may also have load locks at its entrance and exit. If desired, the load locked version may operate a low pressure established by a suitable vacuum pump 210.

Figure 6A:
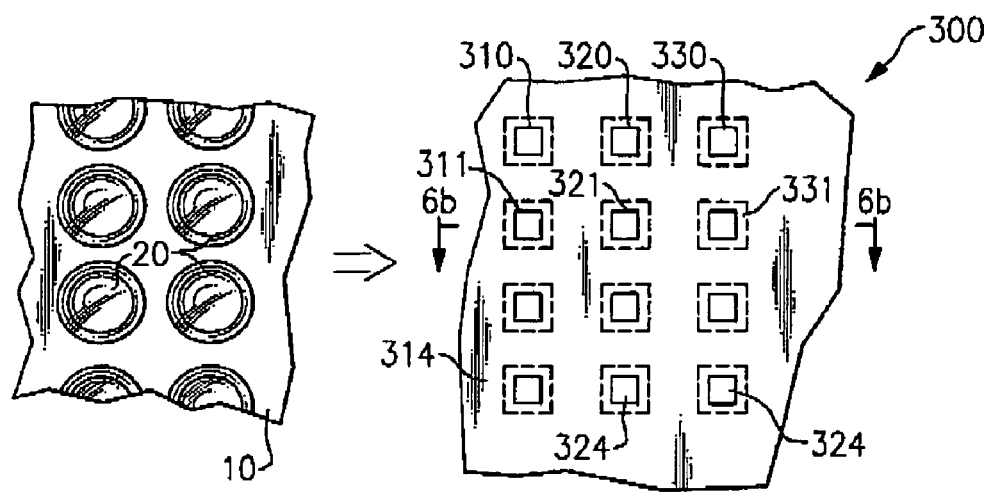
FIGS. 6a, 6b shows steps in a method using an array of plasma generators acting on a corresponding array of lenses.
Figure 6B:
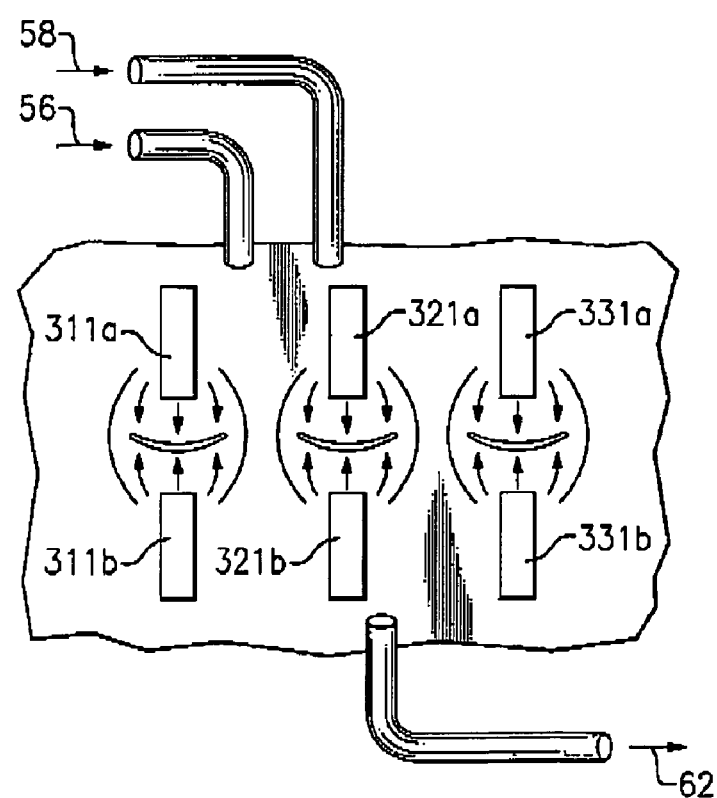

Turing to FIG. 6*a*, there is shown a portion of a conventional holding tray 10 that may hold fifty or more contact lenses. The lenses in the tray have polished edges and they are ready for plasma treatment. In conventional treatment systems multiple trays of lenses would be loaded into a bath plasma processor. Hundreds of lenses would be processes simultaneously. In contrast, the invention uses a conveyor belt or other suitable means (not shown) for carrying a tray into an in-line plasma processor that has a number of plasma generating heads 300. The heads are located above and below each lens so that an upper head and a lower head are associated with each lens. See for example FIG. 6*b* where three pairs of plasma generating heads 311 a, b, 321 a, b and 331 a, b are shown with lenses located between the heads. For a typical tray with fifty lenses, there will be a corresponding number of fifty pairs of plasma generating heads. When the lenses are between the heads, one head in each is selected as an anode and the other head is the cathode. Suitable noble and reactive gases 56, 58 surround the lenses and an applied electric voltage generates plasma for treating the one surface of the lens. Discharge gases 62 are removed. After completion, the polarities of the heads are reversed and the process is repeated to plasma treat the other surface of the lenses. The tray 10 may be made of insulating material, including plastic or glass. The tray may also be made of metal. If the tray 10 is made of metal, it is normally connected to one of the heads during plasma generation. It is preferably connected to the head that serves as the cathode for each operation.

By associating one pair of plasma heads with each lens, the net time to process lenses is reduced compared to the batch process. While one tray is being plasma processed, another tray may be receiving another set of lenses that have their edges polished and clean. When the first tray of lenses is finished with plasma treatment, the next tray is loaded into the process chamber. That chamber may be at atmospheric pressure or reduced pressure. If it is at reduced pressure, then the trays are inserted and removed through conventional load lock entrance and exit chambers (not shown). Those skilled in the art know that items processed in reduced pressure atmospheres may be prepared for insertion and removal by using chambers at the entrance and exit to the reduced process chamber where the items is sealed from atmosphere and lowered to the pressure in the process chamber. Of course, on load lock chamber may perform both functions of lowering and raising pressure while the process chamber is maintained at its lower process treatment pressure.

Having thus described the several embodiments of the invention, those skilled in the art understand that other changes, modifications, additions and deletions may be made to the embodiments without departing from the spirit and scope of the appended claims. For example, the above process and apparatus may be used to apply a plasma surface treatment to intraocular lenses.

The invention claimed is:

1. A method for plasma treating an intraocular or contact lens comprising the steps of:
   supporting a surface of the intraocular or contact lens with a spindle to expose an opposite surface of the lens to a first treatment process;
   using the spindle as one electrode, generating a glow discharge proximate the exposed opposite surface of the lens;
   transferring the lens to an opposite spindle to support the treated opposite surface of the lens and to expose the surface of the lens to a second treatment process; and
   generating a glow discharge proximate the exposed surface of the lens.

2. The method of claim 1 wherein the spindle has a concave surface and the opposite spindle has a convex anterior surface.

3. The method of claim 1 wherein the spindle has a convex surface and the opposite spindle has a concave surface.

4. The method of claim 1 wherein the spindles have supporting surfaces with openings that are connected to conduits for applying a pressure or a vacuum to the lens.

5. The method of claim 1 wherein the plasma treatment is conducted for not more than one minute.

6. The method of claim 5 wherein the plasma treatment is conducted for not more ten seconds.

7. The method of claim 1 further comprising the steps of holding the lens on a spindle and polishing the edges of the lens.

8. The method of claim 1 wherein the step of generating a glow discharge comprises the steps of introducing an inert gas and a reactive gas proximate the exposed surface of the lens and applying a voltage across the lens to generate a plasma proximate the exposed surface.

9. The method of claim 1 wherein the generating of the glow discharge is conducted at atmospheric pressure or reduced pressure.

10. The method of claim 1 wherein the first or the second treatment process includes generating a plasma proximate to the spindles, wherein the area proximate to the spindles comprises an oxidizing atmosphere.

11. The process of claim 1 wherein the spindle or the opposite spindle is one of a plurality of spindles that extend from a transfer plate.

12. The method of claim 1 wherein the first and the second glow discharges are conducted under identical process conditions and the lenses reverse direction along the process path after the transferring of the lenses.

13. A method for plasma treating multiple intraocular lenses or contact lenses comprising the steps of:
   supporting a surface of each lens with a transfer plate to substantially expose an opposite surface of the lens to a treatment process, wherein the transfer plate includes an array of spindles with a concave or convex surface upon which the surface of each lens is supported;
   moving the transfer plate along a process path;
   generating a first glow discharge proximate the process path to treat the exposed opposite surface of the lenses;
   transferring the lenses to an opposite transfer plate to substantially expose the surface, wherein the opposite transfer plate includes an array of opposite spindles with a concave or convex surface upon which the opposite surface of each lens is supported;
   moving the transferred lenses along the process path;
   generating a second glow discharge proximate the process path to treat the surface of each of the lenses.

14. The method of claim 13 wherein the first and the second glow discharges are conducted under identical process conditions and the lenses reverse direction along the process path after the transferring of the lenses.

15. The method of claim 13 wherein the glow discharges are generated by an array of plasma generating heads arranged transverse or parallel to the process path.

16. The method of claim 13 wherein the lenses stop along the process path in the glow discharge for surface treatment.

17. The method of claim 13 wherein the lenses continuously move past the glow discharge.

18. The method of claim 13 wherein the lenses move relative to the glow discharge.

19. The method of claim 13 wherein the lenses and the glow discharge travel together.

20. The method of claim 13 wherein the glow discharge is generated by an array of plasma generating heads.

21. The method of claim 20 wherein the number of plasma generating heads corresponds to the number of lenses simultaneously undergoing plasma treatment.

22. The method of claim 13 wherein the spindles extending from the transfer plate have a convex surface and the opposite spindles extending from the opposite transfer place have a concave surface.

23. The method of claim 13 wherein the spindles extending from the transfer plate have a concave surface and the opposite spindles extending from the opposite transfer plate have a convex surface.

24. The method of claim 13 wherein the steps of generating a glow discharge comprises introducing an inert gas and a reactive gas proximate the exposed surfaces of the lenses and applying a voltage across the lenses to generate a plasma proximate the exposed surfaces.

* * * * *